US010137179B2

(12) United States Patent
Jain

(10) Patent No.: US 10,137,179 B2
(45) Date of Patent: Nov. 27, 2018

(54) COMPOSITION AND METHOD OF PREPARATION OF PROTEASE MICROPARTICULATE SLOW RELEASE PREPARATION

(71) Applicant: Hyalo Technologies, LLC, Mendham, NJ (US)

(72) Inventor: Shalabh Jain, Mendham, NJ (US)

(73) Assignee: HYALO TECHNOLOGIES, LLC, Somerset, NJ (US)

( * ) Notice: Subject to any disclaimer, the term of this patent is extended or adjusted under 35 U.S.C. 154(b) by 227 days.

(21) Appl. No.: 15/157,847

(22) Filed: May 18, 2016

(65) Prior Publication Data

US 2017/0333536 A1    Nov. 23, 2017

(51) Int. Cl.
*A61K 38/48* (2006.01)
*A61K 31/573* (2006.01)
*A61K 47/34* (2017.01)

(52) U.S. Cl.
CPC ........ *A61K 38/4886* (2013.01); *A61K 31/573* (2013.01); *A61K 38/482* (2013.01); *A61K 38/4873* (2013.01); *A61K 47/34* (2013.01); *C12Y 304/21* (2013.01); *C12Y 304/22002* (2013.01); *C12Y 304/24* (2013.01)

(58) Field of Classification Search
CPC ..................................................... A61K 38/48
See application file for complete search history.

(56) References Cited

U.S. PATENT DOCUMENTS

| 6,074,664 A | 6/2000 | Roreger et al. |
| 2012/0101325 A1 | 4/2012 | Lee et al. |
| 2016/0053250 A1 | 2/2016 | Zylberberg et al. |

OTHER PUBLICATIONS

International Search Report and Written Opinion for International Application No. PCT/US2017/032831 (Jul. 31, 2017) (8 Pages).

*Primary Examiner* — Rosanne Kosson
(74) *Attorney, Agent, or Firm* — Lucas & Mercanti, LLP

(57) ABSTRACT

Compositions containing microparticles loaded with one or protease enzymes and optionally auxiliary therapeutic agents and methods of treating conditions such as keloids therewith are disclosed. The biodegradable polymer and the protease enzyme therein form a controlled release matrix for extended release of the enzyme after administration to a mammal in need thereof.

21 Claims, 13 Drawing Sheets

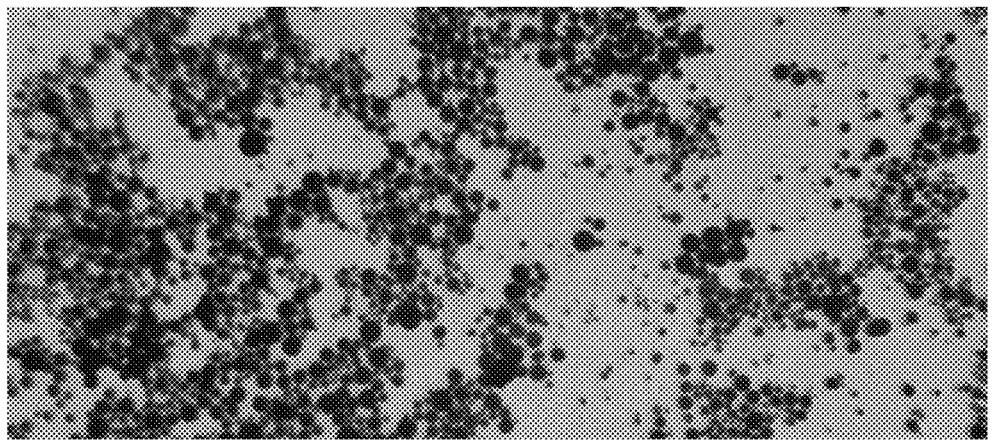
Figure 1: Collagenase Microparticles
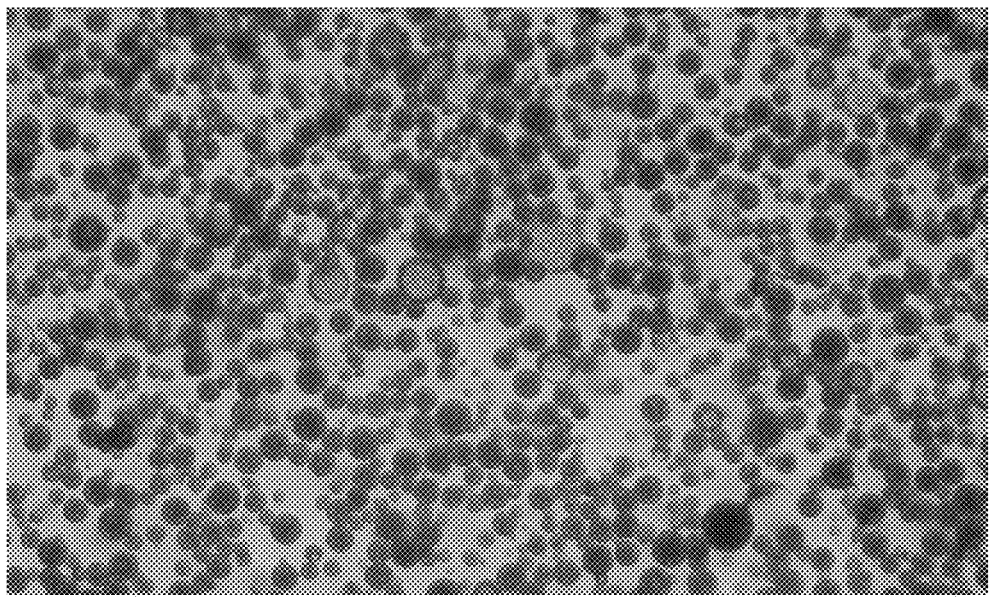
Figure 2: Elastase Microparticles

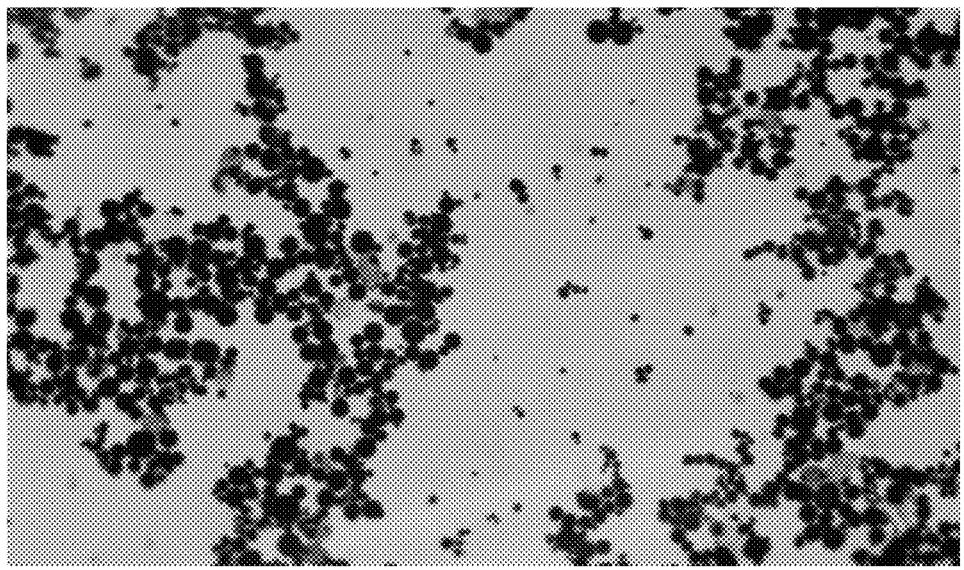
Figure 3: Papain Microparticles
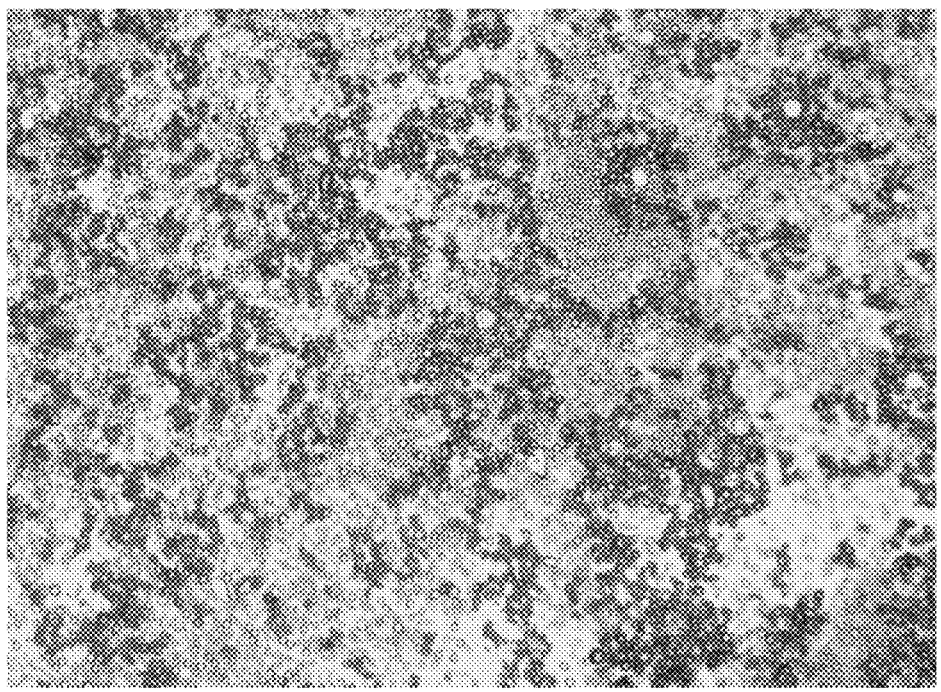
Figure 4: Dexamethasone Microparticles

COMPOSITION AND METHOD OF PREPARATION OF PROTEASE MICROPARTICULATE SLOW RELEASE PREPARATION

BACKGROUND OF THE INVENTION

Scar formation after a surgical procedure or injury is unpredictable and both physicians and patients are highly concerned with minimizing scar appearance. In spite of availability of various in vivo and in vitro studies, limited information is available on the exact cause of scarring. Scaring can lead to the formation of raised nodules called keloids. Scars can also be raised and erythematous in which case they are called hypertrophic scars. Other manifestations of scarring include the formation of adhesions after surgery, frozen shoulder syndrome (from adhesive capsulitis) and acne vulgaris.

Hypertrophic scar formation is often a result of an overproduction and excess deposition of collagen by fibroblasts caused by an increased or prolonged activity of TGF-β1. The surface of the keloid could be smooth, but in most of the cases, it is observed that the keloids are nodular or ridged. This is due to the presence of thickened and hyalinized collagen fibrils, mostly type I and III, which are randomly oriented in case of Keloids. Collagen synthesis in keloids is 3 times greater than in hypertrophic scars and 20 times greater than in normal skin. Adhesive capsulitis is characterized by collagenous tissue associated with fibroblasts and myofibroblasts.

Current treatments for hypertrophic scars and keloids include pressure therapy, silicone based products, radiation therapy, corticosteroid application, cryosurgery and laser surgery. All the above listed treatment options have to be continued over an extended course of time and are expensive and some others pose radiation risks. These treatment modalities are not a permanent cure, and there is a high incidence of recurrence of keloids, with the recurrence rate being reported from 45-100%.

Most therapeutic approaches remain clinically unsatisfactory due to lack of understanding of the physiological processes involved in wound healing and excessive scarring. Currently no successful clinical treatment is available to healthcare providers and patients for conditions with excessive production of collagen. In addition, systemic side effects are high for current treatment options.

Though a number of the treatment strategies have been tried, none of the current treatments are long acting in duration. Use of protease enzymes, including collagenase, papain and elastase as solutions has been reported previously. These systems do not work effectively because the protease activity is self-limiting and is effective for a few hours to 1-2 days only. This is primarily due to the fact that protease enzymes in solution are rapidly degraded by their own activity since all of these enzymes are proteins and hence capable of self-degradation. In addition, once a protease enzyme is in solution form, it is subject to chemical degradation from reactions such as hydrolysis which also results in rapid loss of activity. When protease solutions are injected in the body, the protease are quickly absorbed through the blood or lymph capillaries and removed from the area of injection. This further reduces the amount of protease available at the site of action. Therefore, unless the composition is injected repeatedly over a period of several weeks, the therapy does not work. Since the treatment of scars requires a treatment lasting several weeks or months, there exists a need for a treatment method that does not involve repeated applications or injections of the medicament.

SUMMARY OF THE INVENTION

This invention is based on the discovery that when injected or topically applied protease enzymes are released at a slow rate over a period of time, the enzyme activity is sustained over substantially the entire release time. In accordance therewith, the compositions of the present invention have a release rate for the protease that is high enough to maintain an effective activity of the protease in the application area, yet slow enough to allow continuous presence of protease for many days or weeks.

In one aspect of the invention, there are provided compositions which include a plurality of biodegradable polymer microparticles containing a protease enzyme dispersed or dissolved therein. The biodegradable polymer and the protease enzyme thus form a controlled release matrix for extended release of the enzyme.

In a further aspect of the invention, there is provided an injectable or topical composition of slow release protease that includes the protease enzymes in a matrix which comprises a biodegradable polymer. That is, the matrix includes the polymer in which the protease and/or active medicament is either dispersed or dissolved. In some embodiments, the final form of this composition is a plurality of protease-containing microparticles which can be injected or applied at the site of need.

Each microparticle includes the matrix containing the polymer and the protease and/or active medicament. Once injected or applied to the body, the body fluids around the site of injection penetrate the polymer matrix and begin to degrade the matrix. This results in a controlled release of the entrapped protease enzyme in solution. Since the enzyme trapped in the matrix is in solid form, it is protected from degradation until after it is released. Therefore, a slow release form of protease will sustain its activity at the site of injection or application for the duration of its release. By using a suitable biodegradable polymer, a composition can be fabricated that allows a continuous release of the enzymes over a period of several days, weeks or months.

In another embodiment, there are provided methods of treating hypertrophic scars or hypertrophic tissue in a mammal, preferably a human. The methods include administering an effective amount of the protease-containing microparticles described herein to a mammal in need thereof. The inventive compositions are administered preferably via injection at the site requiring the therapeutic effect. Alternative aspects include topical administration of the protease-containing compositions on the affected areas.

Another aspect of the invention includes the simultaneous use of more than one protease enzyme that works in a synergistic manner to dissolve mammalian scar tissue. These enzymes can be added to the same matrix or be formulated as different matrices and mixed prior to use into a single composition. Suitable protease enzymes can include collagenase, elastase, papain and mixtures thereof.

A still further aspect of the invention is the inclusion of a suitable anti-inflammatory medicament for the purpose of discouraging the formation of additional collagen. One example of this medicament is dexamethasone. This medicament can be included in the microparticle form or as pure drug along with microparticles of the protease enzymes in the composition administered to the mammal in need thereof.

One of the major advantages of this system is its ability to protect the protease enzymes and their activity during the treatment period. This is accomplished by keeping a part of the enzyme in a solid form away from the aqueous environment while release effective concentration of the said enzyme at and around the site of injection or application. The solid form of enzyme protected by the biodegradable polymer is protected from the degrading actions of the body as well as from clearance from the site of application by absorption into circulatory system of blood or lymphatic vessels.

BRIEF DESCRIPTION OF THE DRAWINGS

FIG. 1 shows light microscopic picture of collagenase microparticles prepared according to Example 1 and identified as Composition 1 in Table 1.

FIG. 2 shows light microscopic picture of elastase microparticles prepared according to Example 3 and identified as Composition 9 in Table 1.

FIG. 3 shows light microscopic picture of papain microparticles prepared according to Example 3 and identified as Composition 5 in Table 1.

FIG. 4 shows light microscopic picture of dexamethasone microparticles prepared according to Example 4.

DETAILED DESCRIPTION OF THE INVENTION

Figure 5:
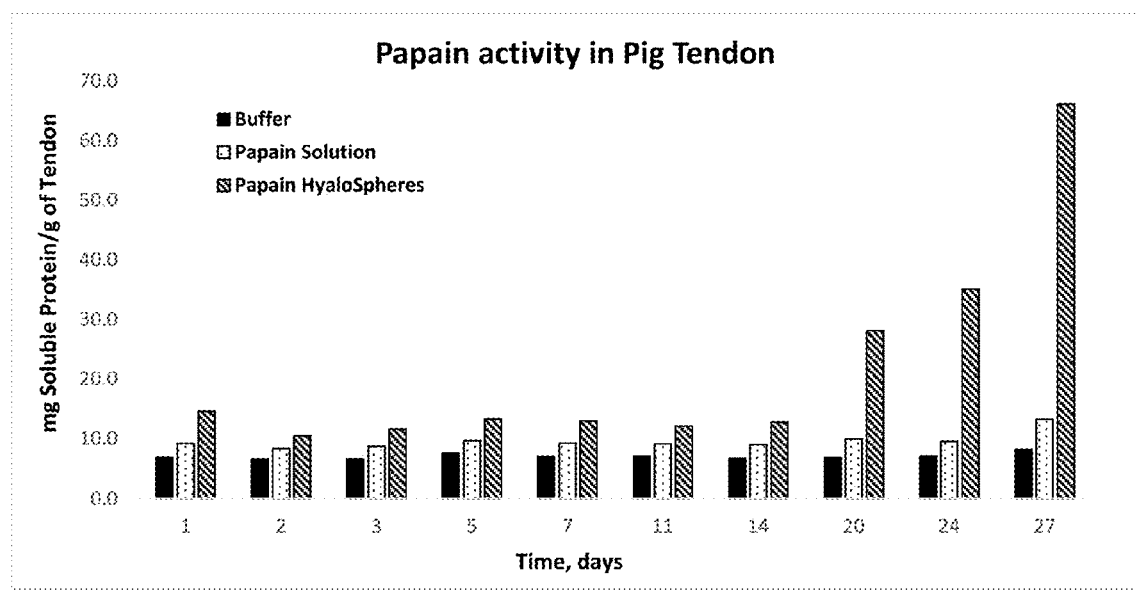
FIG. 5 shows protease activity of papain in solution and microparticle forms on pig tendon tissue as set forth in Example 11. The activity is expressed as the amount of soluble protein per gram of tendon tissue as a function of time.

In some aspects of the invention, there are provided compositions containing a plurality of microparticles containing one or more protease enzymes in order to provide a sustained level of protease activity at the site of injection or application. The composition is based on the discovery that protease enzymes when embedded in a biodegradable polymer matrix release the enzyme at a controlled rate thereby overcoming the problems associated with the current treatment with protease enzymes that rely on injection or application of a solution of the enzymes.

Within this embodiment, the compositions include a plurality of biodegradable polymer microparticles having a protease enzyme therein with the biodegradable polymer and the protease enzyme forming a controlled release matrix for extended release of the enzyme.

For purposes of the present invention, the term "matrix" refers to a microparticle consisting of a suitable polymer in which one or more protease enzymes or other active medicaments are dispersed or dissolved. A plurality of such microparticles for each protease enzyme and anti-inflammatory drug constitute the composition. These compositions containing protease enzymes and anti-inflammatory agent can be combined in various ratios to obtain the final product.

Suitable proteases which can be included in the microparticles and controlled release matrix are generally those capable of having a beneficial effect in the treatment of keloids and/or related hypertrophic scar conditions. In some aspects, the protease is collagenase, in others, the enzyme is papain, while in still other aspects, the enzyme is elastase. The enzymes may be obtained from commercially available sources and/or may be recombinant in origin. For purposes of the present description, protease and enzyme are used interchangeably.

Mixtures of the enzymes in a single controlled release matrix system are contemplated as are compositions containing a blend of two or more different enzyme-containing microparticles. Stated alternatively, it is further contemplated that the compositions described herein will contain a plurality of microparticles include a mixture of microparticles containing different proteases. For example, some compositions will include a first portion of microparticles containing collagenase, and a second portion of microparticles containing papain or elastase. In an alternative embodiment, compositions will contain a first portion of microparticles containing collagenase, a second portion of microparticles containing papain and a third portion of microparticles containing elastase. The ratio of enzyme to enzyme in compositions containing more than enzyme can be broadly expressed as ranging from about 99.9:0.1 to 0.1:99.9. In alternative aspects, the ratio of the enzymes is from about 1:10 to 10:1, with amounts of about 2:1 to 1:2 also being contemplated. The ratio of enzymes can describe either the relative amounts of each enzyme when a combination of enzymes are included in a single controlled release matrix or as a combination of 2 or more types of microparticles, each containing a different enzyme. Those of ordinary skill in the art will, of course, also recognize other beneficial mixtures of proteases in the compositions described herein. It is intended that all such combinations are within the scope of the present invention.

The controlled release matrix included in the inventive compositions includes a biodegradable polymer. While the biodegradable polymer can be selected from a wide variety of polymeric substances, a non-limiting list of suitable polymers which are useful in the formation of the controlled matrix include, without limitation, polymers such as polylactic acid (PLA), polylactic co-glycolic acid (PLGA), polyglycolic acid (PGA) polylactones, polyorthocarbonate, polyhydroxybutyrate, polyalkylcyanoacrylates, polyanhydrides, polyorthoesters, polyester, polyimide, polyglycolides (PGA), polyorthoester, polyacetates, polystyrene, polycarbonates, polysaccharides, polycaprolactone, L-polylactides, block co-polymers of polyesters and linear or star-polyethyleneglycol, poly-beta-hydroxybutyrate, beta-hydroxyvalerate-copolymers, polyaminoacids, hydrophobized hyaluronic acid, dextrans, starches, methyl methacrylate, acrylamide, bisacrylamide, albumin, cellulose, cellulose-based polymers, chitosan, collagen, gelatin, proteins, polyvinyl alcohol (PVA), polyvinylpyrrolidone, polyvinylpyridine, and ethylene glycol polymers. In some preferred aspects of the invention, the biodegradable polymer is a polylactic co-glycolic acid or polylactic acid such as poly lactide-poly glycolide polymer copolymer (PLGA). Thus, some preferred polymers used in the invention are a copolymer of two monomers; lactic acid and glycolic acid. These monomers are combined in a random fashion to produce a polylactic-glycolic acid. For purposes of the present invention, polylactic-glycolic acid and poly lactide-poly glycolide polymer copolymer (PLGA) are used interchangeably. This polymer has been used in various other applications and is approved by the United States Food and Drug Administration (FDA) for use in humans.

The molecular weight for the polymers will vary somewhat depending upon the polymer that is selected. It is contemplated that in certain embodiments, the polymers, such as PLGA will have a molecular weight of from about 7,000 to about 100,000. However, as will be appreciated by those of ordinary skill, all suitable molecular weights are contemplated for any of the polymers included herein.

Formation of the microparticles and controlled release matrices is shown in the examples and in commonly-assigned U.S. patent application Ser. No. 14/600,735, the contents of which are incorporated herein by reference. In some aspects, the resultant microparticles have a cross-sectional diameter of from about 10 nm to about 100 μm. In other aspects, the microparticles have a cross-sectional diameter of from about 100 nm to about 50 μm, while in still others, the microparticles have a cross-sectional diameter of from about 1 μm to about 20 μm. In other embodiments, the polymer matrix containing the polymer and the protease enzymes is prepared as small microparticles in the size range of less than about 1 micrometer to about 50 micrometer or even larger, with a preferred range of size being in the range of about 1-20 micrometers.

The mechanism of release of the proteases from polymers is due at least in part to the erosion of the polymer in an aqueous environment. This erosion varies with the molecular weight of the polymer and the ratio of the lactic acid and glycolic acid monomers. For example, higher lactic acid content for the copolymer with respect to the glycolic acid will extend release of the protease. In such aspects of the invention, ratios of 2:1 or 3:1 are contemplated. The duration of the protease release can also be prolonged by selecting polymers containing esterified end groups or end capped groups.

The amount of protease included in the microparticles can be expressed as percent (%) loading. Generally speaking, the amount of loading can vary depending upon the needs of the artisan, including factors such as the protease or proteases selected for inclusion in the final formulation, the solubility of the desired protease or proteases, the duration and concentration of the protease delivery in vivo, among others. Within this broad range, the percent loading for the protease can range from about 0.1 to about 10%. In other aspects, such as where the protease is collagenase, the percent loading can be from about 3 to about 5%. Similarly, in other aspects, the protease is elastase and the degree of loading is from about 0.1. Alternatively, the protease can be papain and the degree of loading can be from about 0.5 to about 0.9%. In alternative embodiments, however, the microparticles can contain higher amounts of a protease enzyme. For example, higher loadings of enzymes, e.g. up to 50% or more than the amounts set forth above, can be achieved by using one or a combination of techniques such micronized protease suspensions and/or by varying the aqueous solvents, i.e. altering pH by 1-2 units, used to prepare the loaded microparticles. Such variations and different loading amounts of protease enzymes are therefore included in the scope of this invention.

In further embodiments of the invention, the compositions may include an auxiliary therapeutic agent. The agent may be within the biodegradable polymer matrix, that is part of the microparticle matrix or added to the composition separately. The auxiliary therapeutic agent can be any therapeutic substance or medicament which enhances treatment with the protease. For example, the auxiliary therapeutic agent can be a steroidal or a non-steroidal inflammation reducing agent such as dexamethasone, corticosteroids such as prednisone, methylprednisolone, etc. and other agents well known to those of ordinary skill. Other examples of auxiliary therapeutic agents include, for example, anti-neoplastic agents such as sirolimus and tacrolimus, and other immunosuppressant agents. Dexamethasone is a preferred auxiliary therapeutic agent for inclusion in the compositions described herein. The amount of the auxiliary agent included in the composition will be understood to be an effective amount and will depend upon the agent selected. For purposes of the present invention, an effective amount shall be understood to be an amount which is sufficient to enhance the therapeutic effect of the protease(s). It is contemplated that the auxiliary agents will be present in amounts of from 0.001 to about 10% by weight of compositions.

In those embodiments where the composition of the invention is combined with additional therapeutic entities such as anti-inflammatory agents to further increase its efficacy, a purpose for doing so is to minimize the inflammation at the site of hypertrophic scarring. Inflammation is believed to be a contributing factor in overproduction of collagen in these conditions. As mentioned above, the anti-inflammatory agent can be incorporated in the microparticles containing one or more protease enzymes, or it can be included as a separated microparticle system mixed with the microparticles of the protease enzymes.

Compositions/Formulations

Pharmaceutical compositions containing the protease containing microparticles described herein may be manufactured by processes well known in the art. The compositions containing the microparticles may be formulated in conjunction with one or more physiologically acceptable carriers comprising excipients and auxiliaries which facilitate processing of the microparticles into final formulations or preparations which can be used pharmaceutically. It is contemplated that the compositions will in some embodiments be provided in pre-filled syringes containing an amount of the inventive compositions for a single or unit dose. Proper formulation is dependent upon the route of administration chosen, i.e. injection or topical administration.

For injection, including, subcutaneous injection, the microparticles of the invention may be formulated as part of an aqueous suspension, and may preferably include physiologically compatible preservatives, buffers, etc. Aqueous injection suspensions may also contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the microparticles may be lyophilized in powder form for constitution with a suitable vehicle, e.g., sterile, pyrogen-free water, before use.

The microparticles of the invention may also be formulated in topical compositions such as creams or ointments, using, e.g., conventional excipients and bases such as petrolatum, etc.

Methods of Treatment

In yet another aspect, the present invention provides methods of treating hypertrophic scars (or tissue) in a mammal. The methods include administering an effective amount of a composition containing the protease microparticles described herein to a patient, i.e. mammal or human in need thereof. In alternative aspects, the methods of treatment using the compositions described herein generally include any condition calling for administration of a protease. In many aspects of the invention, the hypertrophic scar is a keloid and the treatment is carried out by injecting the composition to an area requiring the treatment. Alternatively, the administering of the compositions described herein is carried out by topically applying the composition to an affected area. Determination of a therapeutically effective amount is well within the capability of those skilled in the art, especially in light of the disclosure herein. Moreover, the amount required for each administration will vary somewhat depending upon the protease or proteases selected and the type of polymeric matrix used. For example, in some aspects of the invention the compositions are administered by injection at the site of need. i.e. intra-lesionally, once a week. In other aspects, the composition is administered once a month or every two months.

Generally speaking, it is contemplated that administration of compositions capable of delivering from about 25 U to about 200 U of collagenase, about 0.05 U to about 2.0 U of elastase and from about 0.2 U to about 5.0 U of papain per administration as needed or until the desired improvement in the condition being treated is observed. Based on the units/mg activity values provided by the supplier, these concentrations correspond to about 200 micrograms/ml to about 1600 micrograms/ml of collagenase, about 12.5 micrograms/ml to about 500 micrograms/ml of elastase and from about 10 micrograms/ml to about 250 micrograms/ml of papain per administration as needed or until the desired improvement in the condition being treated is observed. These concentrations will vary somewhat according to the specific condition and size of the treatment area and such variations will be apparent to those of ordinary skill without undue experimentation.

One use of this invention is in the treatment of hypertrophic scars resulting from a variety of reasons. These reasons include post-surgical scars, wounds from injury or burns, formation of keloids, scarring due to acne and related conditions and tissue adhesion in the organs. Further, it has been discovered that protease enzymes when injected or applied in a slow release form in combination with each other work in a synergistic fashion, thereby exerting a higher degree of protease activity than is expected from application of a single protease enzyme. This invention allows one to produce a customized combination of the slow release microparticle form of protease by mixing individual enzyme microparticles in various proportions. This is a distinct advantage over the existing systems because it allows customization of the composition to overcome the need for individual disease condition.

EXAMPLES

The following examples serve to provide further appreciation of the invention but are not meant in any way to restrict the effective scope of the invention.

Methods of Preparing Compositions

Example 1

Preparation of Collagenase Microparticles 0.5 gram of polylactic co-glycolic acid polymer (called 1A) with an average molecular weight of about 10 kilo Dalton and which consisted of a 50:50 mixture of lactic acid and glycolic acid monomers is dissolved in 10 milliliters of dichloromethane. In a separate vessel, 20 milligrams of collagenase powder is added to 0.5 milliliter of purified water to obtain a clear solution. This solution is filtered through a 0.2 micron filter to remove any insoluble material. 0.4 milliliters of the filtered protease solution is added to the polymer solution. This mixture is vortexed at a high rate for 60 seconds to disperse the protease solution in the polymer solution. The dispersion is sonicated using a 3 mm sonication tip at 40% amplitude for 60 seconds to prepare a fine emulsion containing the protease solution emulsified in the polymer solution. This first emulsion is added to 40 milliliters of a 2% solution of polyvinyl alcohol (PVA) in water. A homogenizer with 7 mm tip is dipped in the above mixture and the mixture is homogenized at a setting of 3 for 90 seconds to obtain a second emulsion. This second emulsion is poured in a beaker containing 200 milliliters of purified water stirred by a magnetic stirrer. The mixture is stirred at room temperature for 4 hours to allow evaporation of dichloromethane.

The above mixture is transferred to large centrifuge tubes and subjected to centrifugation for 5 minutes to concentrate the particles as a pellet at the bottom of the tubes. The concentrated particles are pooled in a single tube and washed 3 times with purified water to remove excess PVA solution. Washings are carried out by adding 20 milliliters of purified water, vortexing for 10 seconds, followed by centrifugation. After the final washing, the particle pellet is washed out in a glass vial using about 2 milliliters of purified water and frozen at −40° C. See FIG. 1. The process of this example was repeated two further times to provide Compositions 3 and 4 mentioned in Table 1 below.

Example 2

Preparation of Papain and Elastase Microparticles

Papain and elastase microparticles were made following the process of example 1 except that 10 mg each of these enzymes was added to purified water followed by stirring at 37° C. for one hour. This mixture was filtered through a 0.2 micron syringe filter to remove undissolved enzyme. The filtered solution was used to prepare the microparticles as described in example 1 starting with the vortexing step.

The processes of this example were repeated two further times to provide Compositions 6 and 8 for papain and Compositions 10 and 12 for elastase mentioned in Table 1 below.

Example 3

Collagenase, papain and elastase microparticles were made following the processes of Examples 1 and 2, except that the polylactic co-glycolic acid polymer is listed as grade 3A and has an average molecular weight of about 25 kilo Dalton. The compositions are identified below in Table 1 as Composition Numbers 2, 5 and 9 respectively. See FIGS. 2 and 3

Example 4

Preparation of Dexamethasone Particles 0.5 grams of the polylactic co-glycolic acid polymer used in Example 1 is dissolved in a mixture of 14 milliliters of dichloromethane and 7 milliliters of ethyl alcohol. 100 mg of dexamethasone are added to this mixture in a 50 ml tube. 30 milliliters of 4% PVA solution are added to the tube, followed by vortexing for 30 seconds. The mixture is then homogenized using a 7 mm tip at setting of 2 for 30 seconds. The mixture is immediately poured in 60 milliliters of purified water in a beaker and stirred with a magnetic stirrer for 4 hours.

The above mixture is transferred to large centrifuge tubes and subjected to centrifugation for 5 minutes to concentrate the particles as a pellet at the bottom of the tubes. The concentrated particles are pooled in a single tube and washed 3 times with purified water to remove excess PVA solution. Washings are carried out by adding 20 milliliters of purified water, vortexing for 10 seconds, followed by centrifugation. After the final washing, the particle pellet is washed out in a glass vial using about 2 milliliters of purified water and frozen at −40° C. See FIG. 4.

Example 5

Freeze Drying of Particles

The material of Examples 1-4 was subject to freeze drying by applying a vacuum of less than 200 millitorrs for 24 hours while the temperature of the vial was maintained at 0° C. Following this initial phase of drying, the temperature of the vial was increased to 25° C. and vacuum continued for another 2 hours. The vial was then removed from the freeze dryer and the material was removed with a spatula and mixed to obtain a uniform solid material. The material was transferred to a weighing paper and weighed to calculate the yield.

Determination of Drug Loading in the Microparticles

Example 6

Drug Loading of Protease Enzymes 5 mg of accurately weighed microparticles were added to 5 milliliters of dichloromethane in a 50 ml tube. As a reference, 5 mg of polymer and about 1 mg of each enzyme was added to another tube in 5 milliliters of dichloromethane. A blank was prepared by adding 5 mg of polymer to a tube in 5 milliliters of dichloromethane. The mixtures were stirred until the microparticles and the polymer dissolved. To each tube, 10 milliliters of purified water was added followed by vortexing at high speed for 60 seconds. The mixtures were allowed to stand at room temperature for 15 minutes followed by centrifugation for 2 minutes. 100 microliters of the aqueous layer was transferred from each tube to a labeled vial and diluted with 900 ul of purified water. These solutions were subjected to a protein assay using the BCA assay protocol using bovine serum albumin as protein standards. Protein content in the microparticles was determined from this procedure and the value was used to calculate the loading efficiency (percent of total added enzyme incorporated in the polymer) and percent loading (protein content as percent of total weight of microparticles).

Example 7

Drug Loading of Dexamethasone 15 milligrams of accurately weighed dexamethasone microparticles were added to 5 milliliters of 0.1 molar sodium hydroxide solution in a labeled vial. This vial was subjected to gentle shaking at 37° C. for 24 hours. 5 milligrams of dexamethasone powder was similarly processed as a standard sample. After shaking, the samples were cooled to room temperature and 10 milliliters of methyl alcohol was added to each vial. This solution was centrifuged at 2000 g for 3 minutes. 100 microliters of the supernatant from the vials was diluted with 900 microliters of methyl alcohol. Absorbance of these solutions was read at 240 nm in a UV spectrophotometer. The amount of dexamethasone in microparticles was calculated by comparing the absorbance with the standard containing 5 milligrams of dexamethasone. Percent loading of dexamethasone was calculated based on the amount of dexamethasone in the microparticles.

Example 8

Microscopic Examination and Size Measurement

About 5 milligram of microparticles was suspended in 100 microliters of purified water. A drop of this suspension was placed on a clean glass slide and spread as a thin layer. The layer was observed under the microscope. Digital pictures were taken for the microparticles and the diameter of 20 microparticles in a set field was measured to calculate the average diameter of the particles.

TABLE 1 composition, percent yield and drug loading of microparticles

| Composition # | Material | Polymer grade | Average diameter Micrometers | % Yield | % drug loading |
|---|---|---|---|---|---|
| 1 | Collagenase | 1A | 11 | 59 | 3.6 |
| 2 | Collagenase | 3A | 10 | 50 | 4.91 |
| 3 | Collagenase | 1A | 12 | 68 | 4.06 |
| 4 | Collagenase | 1A | 11 | 81 | 3.85 |
| 5 | Papain | 3A | 11 | 69 | 0.82 |
| 6 | Papain | 1A | 9 | 65 | 0.68 |
| 7 | Papain | 1A | 9 | 58 | 0.59 |
| 8 | Papain | 1A | 5 | 72 | 0.66 |
| 9 | Elastase | 3A | 6 | 36 | 0.49 |
| 10 | Elastase | 1A | 6 | 59 | 0.21 |
| 11 | Elastase | 1A | 6 | 52 | 0.16 |
| 12 | Elastase | 1A | 9 | 50 | 0.17 |

As seen in Table 1, the amount of protease enzymes in the microspheres calculated as percent on w/w basis ranges from 0.16 to 4.91. This amount varies for each protease enzyme, ranging from 0.16-0.49 for elastase, 0.59-0.82 for papain, and 3.60-4.91 for collagenase. This difference in percent content of protease enzymes is due to different solubility of these enzymes in water or buffer solution. Collagenase being highly soluble can be loaded in higher concentration.

Example 9

Tissue Preparation

A. Pig Tendon

Fresh pig feet were washed with phosphate buffer saline solution containing 0.2% sodium azide as preservative. Tendons in the feet were removed with scissors and were scrapped with a sharp razor blade to remove any remnants of muscle and fat. The cleaned tendons were cut into pieces weighing about 20 mg each. These pieces were added to enough volume of phosphate buffer saline solution containing 0.2% sodium azide in a beaker to cover the tissue and the mixture was stirred for 12 hours to remove any soluble protein. The buffer was decanted from the beaker, replaced with fresh buffer, stirred for 5 minutes and decanted again. This process was repeated 2 more times to thoroughly wash the tissue. The washed tissue was transferred to a stainless steel tray and blotted with a clean lint free tissue paper to remove excess liquid. The tissue was then weighed in individual labeled tubes for protease activity studies.

B. Dermal Collagen

Fresh pig skin was excised from the pig feet in about 2 square inch sections. The skin was washed with phosphate buffer saline solution containing 0.2% sodium azide as preservative and kept soaked in the buffer solution when not being processed. The dermal collagen was removed by carefully scrapping about 2 mm thick layer of the skin from the dermal tissue. This tissue was pooled in a beaker containing enough volume of phosphate buffer saline solution containing 0.2% sodium azide and the mixture was stirred for 12 hours to remove any soluble protein. The buffer was decanted from the beaker, replaced with fresh buffer, stirred for 5 minutes and decanted again. This process was repeated 2 more times to thoroughly wash the tissue. The washed tissue was transferred to a stainless steel tray and blotted with a clean lint free tissue paper to remove excess liquid. The tissue was then weighed in individual labeled tubes for protease activity studies.

C. Pig Skin

Fresh pig skin was excised from the pig feet in about 2 square inch sections. The skin was washed with phosphate buffer saline solution containing 0.2% sodium azide as preservative and kept soaked in the buffer solution when not being processed. For protease studies, the skin was cut into square pieces measuring about 4 square millimeters. This tissue was pooled in a beaker containing enough volume of phosphate buffer saline solution containing 0.2% sodium azide and the mixture was stirred for 12 hours to remove any soluble protein. The buffer was decanted from the beaker, replaced with fresh buffer, stirred for 5 minutes and decanted again. This process was repeated 2 more times to thoroughly wash the tissue. The washed tissue was transferred to a stainless steel tray and blotted with a clean lint free tissue paper to remove excess liquid. The tissue was then weighed in individual labeled tubes for protease activity studies.

D. Lyophilized Collagen

Lyophilized bovine collagen was obtained from commercial sources. This collagen is a pure form of collagen and was used as received. For protease activity studies, the collagen fibers were weighed as dry material into individual tubes followed by the addition of protease solutions or microparticles.

Example 10

Protease Activity Protocol

All tissues were prepared fresh for each study as described above. Stock solutions of each protease enzyme were prepared in the buffer at a concentration of 100-500 ug/ml. Appropriate volume of each solution was added to a 2 milliliter tube to allow the final concentration to be at the desired level as mentioned in Table 2 (below in Example 13) after the volume in the tube was made up to 1 milliliter using the buffer. The buffer contained a 0.2% concentration of sodium azide to protect from microbial growth. Microparticles were suspended in the buffer solution at a concentration of 150 milligrams in 4.5 milliliters. 0.5 milliliters of this suspension was added to each tube to obtain the final concentration of 15.5 mg/ml of each microparticle. Table 2 contains the details of each protease and its microparticle concentration in the study. All studies were set up by mixing appropriate volumes of the stock solutions of protease in solution and microparticle form with enough volume of buffer to have a final volume of 1 milliliter.

Once all samples were prepared, the tubes were loaded on the racks and placed in an incubator containing a rotary shaker. The temperature in the incubator was maintained at 37° C. and the racks were stirred at 100 rpm in a rotary shaker. The samples were continuously stirred during the entire duration of study except when they were removed for sampling. All studies were carried out in duplicate and the values reported are an average of the two values.

At the designated time points, the tubes were removed from the rack and were subjected to centrifugation at 2000 g for 3 minutes. The tubes were opened and a 10 microliter sample of clear supernatant solution was transferred to a labeled 96-well plate. The tubes were then sealed and replaced in the incubator.

The content of free (soluble) protein in samples removed from the tubes was measured using a commercially available BCA protein assay kit. Bovine serum albumin (BSA) was used as a standard protein. Several concentrations of BSA were prepared for this purpose in order to obtain a regression line for the standard curve. The regression equation was used to calculate the concentration of soluble protein in each sample. The protein content in each tube was determined based on the volume of the solution in the tube and the protein concentration. Since successive sampling reduces the volume in each tube by 10 microliters, all protein content values were corrected for this volume change. Cumulative amount of soluble protein in each sample was obtained and was normalized for the weight of the tissue. The final protein content was calculated as milligrams of soluble protein for one gram of the tissue in the sample.

Example 11

In order to study the efficacy of the compositions of the invention relative to the injection or application of a solution of the same protease enzymes, the protease enzymatic activity of the prepared microparticles was studies in a variety of tissues and materials. The materials used in this study include a pure form of collagen obtained from bovine sources. The tissues included in this study include the whole skin of pig, tendon from pig and the dermal collagen from pig. Pig skin has been extensively used as a model for screening of therapeutic agents for use in humans. The selection of these tissues was based on their collagen content. Pig tendon consists almost entirely of type 1 collagen with small amounts of type 3 collagen. Skin dermal collagen is a good model for studying the activity of protease enzymes because it mimics the type of collagen matrix found in hypertrophic scars and keloids. In addition, whole skin of pig was included to study the effect of the composition on the entire organ.

Preliminary studies were carried out using the pure bovine collagen to select appropriate concentration of each protease enzyme. The enzyme activity was determined by a method developed in our laboratory to study the conversion of native collagen into a soluble form of protein that can be absorbed by the body. Native collagen is practically insoluble in body fluids and other aqueous solutions similar to body fluids. When collagen in any form is suspended in an aqueous solution of pH (pH value of 7.4) close to the body fluids, it is insoluble and stays insoluble over a period of several weeks. When a clear sample of this suspension is analyzed for soluble protein content, the amount of soluble protein content does not change over a period of several weeks as shown in FIG. 5. The amount of soluble protein in buffer without any protease is within the experimental variation of the soluble protein content over a period of 27 days. However, when a protease is added to the suspension, the protease activity begins to degrade the insoluble collagen into soluble protein, thereby increasing the amount of soluble protein in the solution phase of the suspension.

As seen in FIG. 5, in the presence of papain solution, the amount of soluble protein increases steadily over a period of about 4 weeks. The soluble (also called as free protein) can be measured by a variety of protein assay methods. The method used in this study is called as the BCA protein assay kit that is commercially available from several sources. This assay can reliably measure the soluble protein amount in an aqueous system at concentrations ranging from a few micrograms to several hundred micrograms per milliliter.

FIG. 5 also shows that the activity of papain in microparticle form has much higher activity against collagen in the tendon tissue. As a comparison, the amount of soluble protein present in the sample increases by 300% with papain microparticles when compared with the papain solution.

As seen in FIG. 5 when pig tendon was exposed to buffer, there was no significant increase in the amount of soluble protein the solution phase of the tendon suspension over a period of about 4 weeks. This amount stays in range of 6-10 milligrams of protein per gram of tendon tissue. When papain enzyme at a concentration of 100 micrograms per milliliter is added to the suspension, the amount of soluble protein increases steadily over a period of about 4 weeks. After 27 days, the total amount of soluble protein in the solution phase is about 14 milligrams per gram of tendon tissue. However when papain microparticles are added to the suspension without the papain solution, the amount of soluble protein increases at a much faster rate. At 27 days, the amount of soluble protein is about 65 milligrams per gram of tendon tissue. Since the only source of soluble protein the solution is from degradation of collagen in the tendon, the soluble protein amount correlates with degradation of the collagen in tendon tissue, and hence with protease activity of the enzyme. The microparticles show approximately 450% increase in the extent of collagen degradation when papain is added as microparticle composition described in this invention.

Example 12

Figure 6:
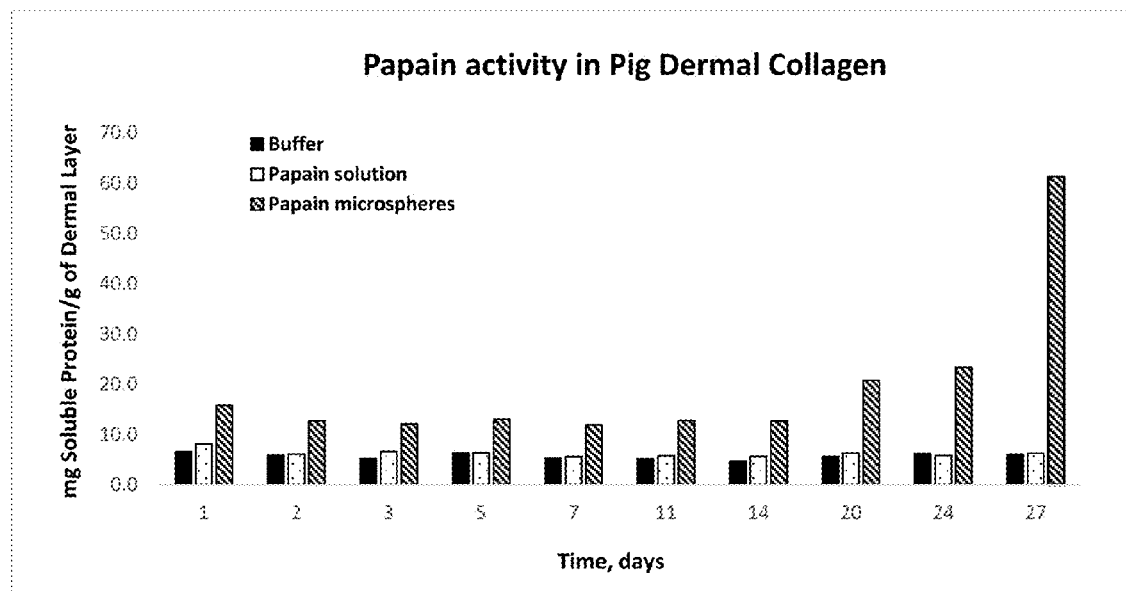
FIG. 6 shows protease activity of papain in solution and microparticle forms on pig dermal collagen as set forth in Example 12.

In order to confirm that these results are due to protease activity on collagen tissue, the study was repeated on collagen tissue harvested from dermal layer of the pig skin as described in Example 9B. Similar results can be seen with the collagen from dermal layer as shown in FIG. 6. The amount of soluble protein produced in this study after about 4 weeks is about 700% higher from the microparticle form of papain compared with the solution form of papain. The results of this example also confirm that the composition described in this invention is effective on collagen from more than one source or organ.

Example 13

Figure 7:
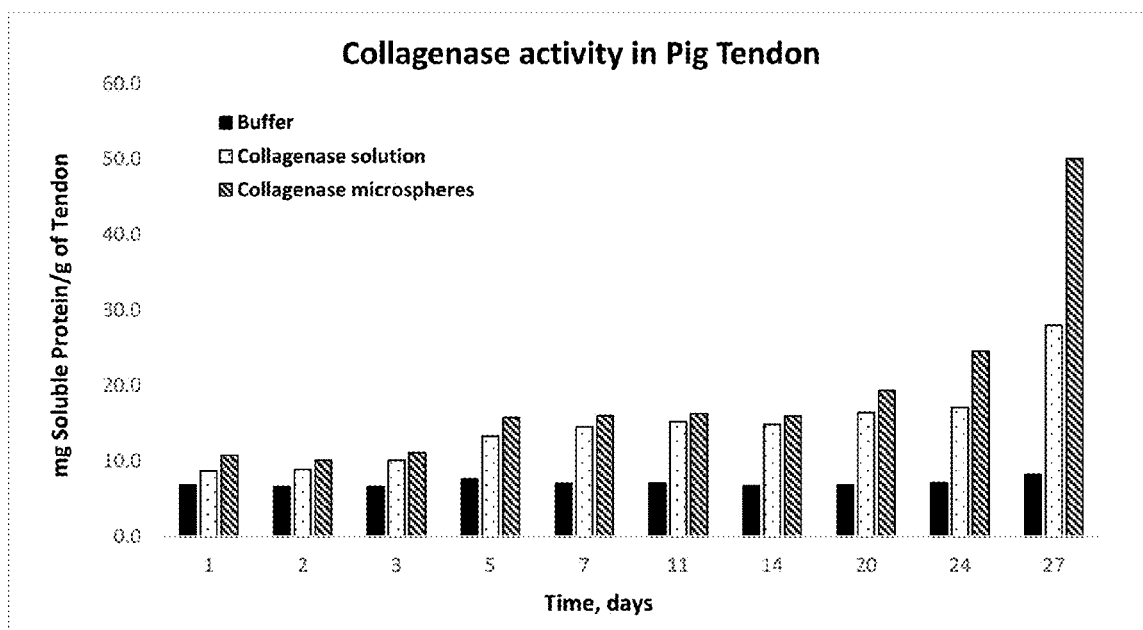
FIG. 7 shows protease activity of collagenase in solution and microparticle forms on pig tendon tissue as set forth in Example 13.
Figure 8:
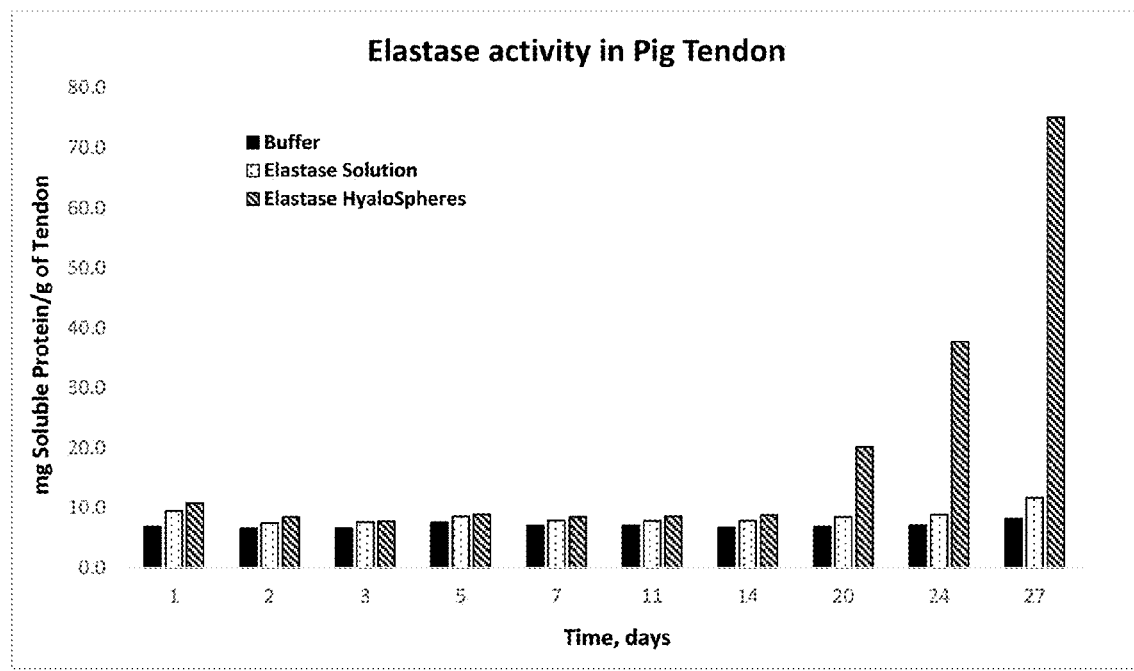
FIG. 8 shows protease activity of elastase in solution and microparticle forms on pig tendon tissue as set forth in Example 13.

Similar results can be seen in FIG. 7 where addition of collagenase enzyme as microparticles results in 880% and 178% increase in the extent of collagen degradation compared with buffer and collagen solution, respectively. Similarly, as shown in FIG. 8, elastase enzyme results in 1200% and 584% increase in the extent of collagen degradation compared with buffer and collagen solution, respectively. These results clearly show that application of protease enzymes as composition of this invention offers significant advantage in degrading collagen.

In the above studies, the elastase and collagenase enzymes were added as solutions in the concentration of 100 micrograms per milliliter. 15 milligrams of microparticles of each enzyme were added in the microparticle study. Based on average percent enzyme loading in microparticles (calculated as percent of protease enzyme in total amount of microparticles on w/w basis) (0.52% and 0.70% of enzyme in the microparticles for elastase and papain, respectively) the total amount of elastase and papain added as microparticles were 61 and 105 micrograms, respectively. Since the release of these enzymes is typically linear with time from the microparticles, their average concentration in the solution can be approximated by half of the total amount added, assuming that all the enzyme is released in 27 days. When the data is normalized to the average amount of protease in solution from microparticles (expressed as µg soluble protein/g tissue/µg enzyme), elastase and papain microparticles increase the amount of collagen degradation by 1016% and 484%, respectively. For collagenase, there is a decrease of 86% in collagen degradation when the data is normalized to total amount of protease in the solution. Although this decrease is observed, the overall advantage of collagenase on collagen degradation can be obtained by adding proportionately larger amount of collagen in microparticle form. Further, it can be noted that the extent of collagen degradation in collagen solution treated studies from day 14 to day 27 increases by 1.89 fold, while the corresponding value for collagen in microparticle form when normalized for protease amount is 4 fold. Therefore, it is clear that over a period of about 4 weeks, all protease enzymes perform significantly better when used as composition of this invention compared with the solutions of the protease.

It must be noted that in these studies, none of the protease solutions are removed from contact with the tissue because there is no clearance of protease from the suspensions. In a biological system, the soluble part of the protease will be removed by absorption in the circulatory system whereas the rate of removal from microparticle form will be smaller due to the fact that most of the protease is protected by the polymer matrix. This will result in a much higher efficacy of protease enzymes in an in-vivo situation.

The above studies were carried out for all protease enzymes for 3 different sources of collagen. These sources included pig tendon, whole pig skin and the dermal layer of pig skin. The results of these studies are summarized in Table 2.

TABLE 2

Comparison of protease activity in microparticle and solution forms in different collagen tissues

| Tissue | Compositions | Protease Enzymes | Protease conc. ug/ml* | Protease conc. units/ml** | Percent increase Days 1-27 | Ratio Microspheres/Solution |
|---|---|---|---|---|---|---|
| Tendon | Solutions | Collagenase | 10 | 1.25 | 222.6 | |
| | | Elastase | 50 | 0.2 | 22.8 | |
| | | Papain | 50 | 1.05 | 44.2 | |
| | Microparticles | Collagenase | 600 | 75 | 365.7 | 1.6 |
| | | Elastase | 45 | 0.18 | 599.4 | 26.3 |
| | | Papain | 90 | 1.87 | 352.4 | 8.0 |
| Skin | Solutions | Collagenase | 10 | 1.25 | 154.9 | |
| | | Elastase | 50 | 0.2 | 47.3 | |
| | | Papain | 50 | 1.05 | 40.8 | |
| | Microparticles | Collagenase | 600 | 75 | 465.6 | 3.0 |
| | | Elastase | 45 | 0.18 | 600.3 | 12.7 |
| | | Papain | 90 | 1.87 | 253.9 | 6.2 |
| Dermal Layer | Solutions | Collagenase | 10 | 1.25 | 46.3 | |
| | | Elastase | 50 | 0.2 | −18.1 | |
| | | Papain | 50 | 1.05 | −22.6 | |
| | Microparticles | Collagenase | 600 | 75 | 50.8 | 1.1 |
| | | Elastase | 45 | 0.18 | 596.6 | high |
| | | Papain | 90 | 1.87 | 287.8 | high |

*protease amount in microparticles calculated from percent loading of enzymes
**units/ml calculations based on vendor supplied enzymes activity (units/mg)

This table shows that there is an increase ranging from about 50% to about 600% for all protease enzymes in tendon and skin tissues when compared with exposure of the tissues to buffer alone. In the dermal layer, elastase and papain enzymes show no significant increase in protease activity when added to the tissue as solutions. The microparticle containing proteases on the other hand did. In order to assess the relative activity of enzymes in microparticle and solution forms, a ratio of the protease activity is calculated by dividing the activity from microparticles with activity from solution. As seen in the Table, this ratio ranges from 1.6 to 26.3 for collagen tissue, similar results are observed for the other tissues as well. Therefore it can be concluded that microparticle form of enzymes performed significantly better in all tissues.

Example 14

Figure 9:
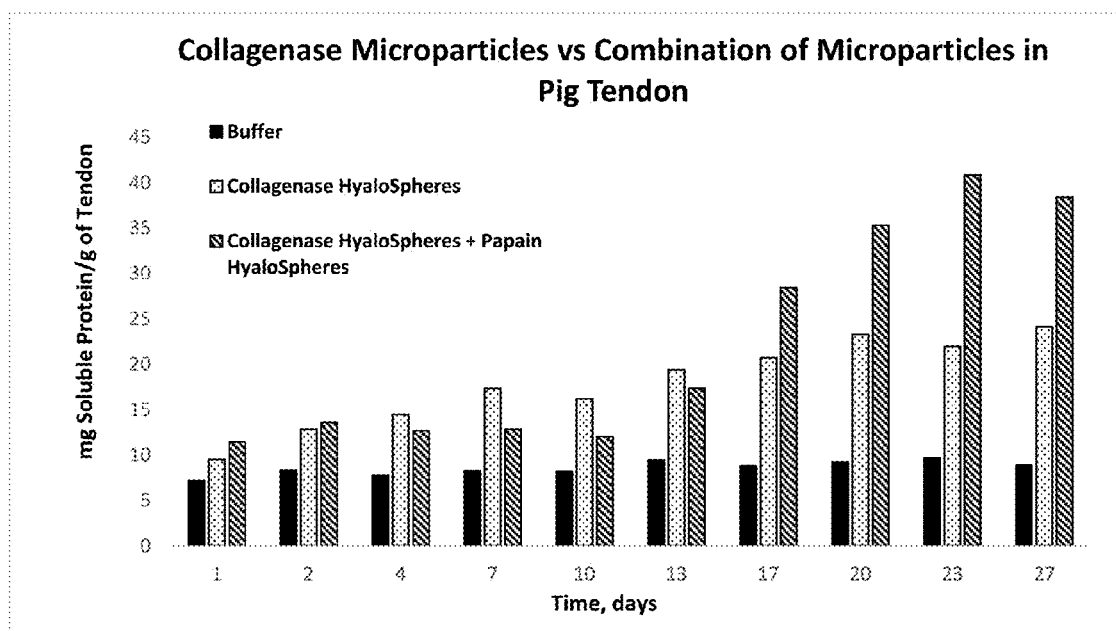
FIG. 9 shows protease activity of collagenase microparticles alone and a combination of collagenase microparticles and papain microparticles on pig tendon tissue as set forth in Example 14.
Figure 10:
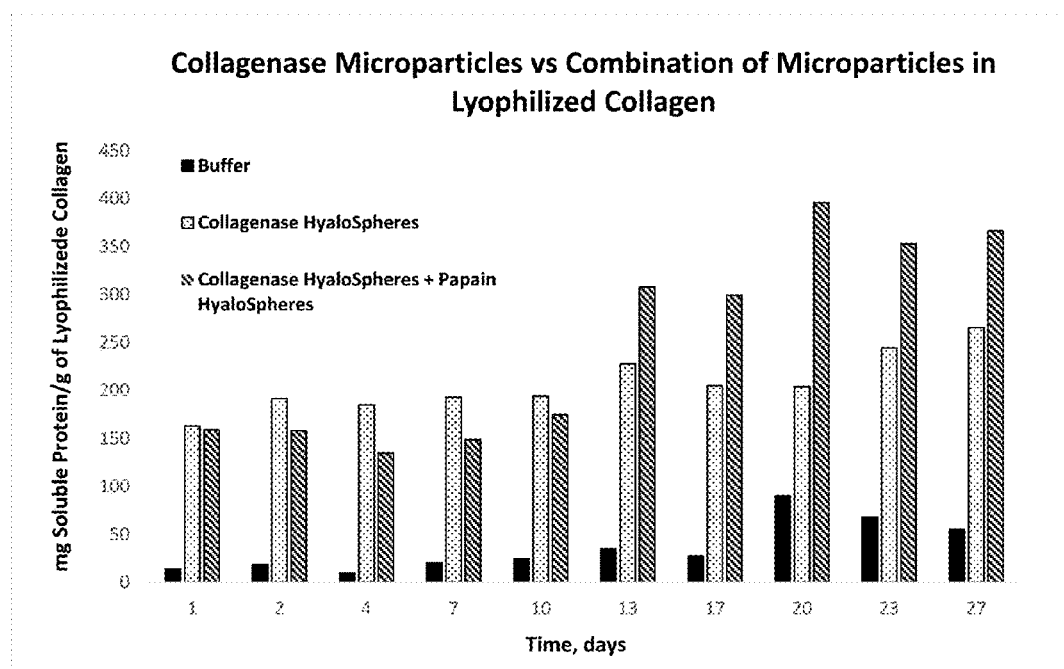
FIG. 10 shows protease activity of collagenase microparticles alone and a combination of collagenase microparticles and papain microparticles on bovine collagen tissue as set forth in Example 14.

In order to study the possible synergistic action of protease enzymes from microparticle compositions, various combinations of enzyme containing microparticles were studies in a similar way as the above studies in pig tendon and bovine collagen. As seen in FIG. 9, when collagenase and papain microparticles are added together to the pig tendon tissue, the resulting protease enzymatic activity is higher than the activity of individual enzymes. This shows that there is a synergistic action of the enzymes in microparticle form. In order to confirm that this phenomenon occurs in collagen from other sources as well, this study was also carried out on lyophilized form of bovine collagen. As shown in FIG. 10, the results are very similar to the ones in FIG. 9, confirming a synergistic action of the two enzymes in microparticle form.

Example 15

Figure 11:
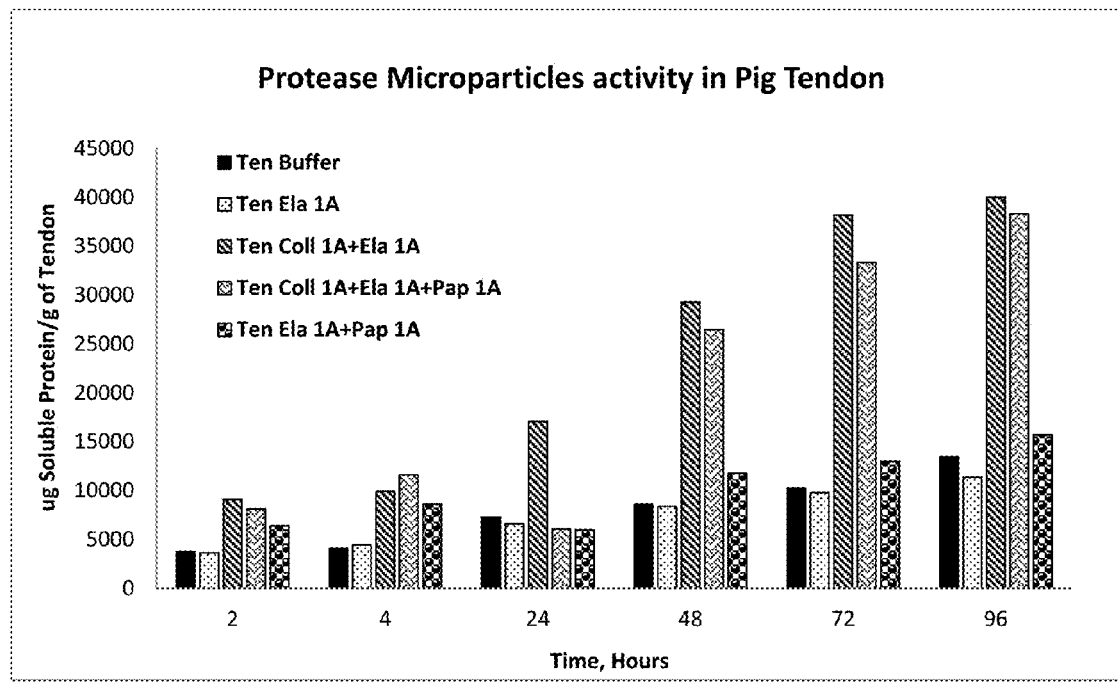
FIG. 11 shows protease activity of elastase microparticles alone and in combination with other protease containing microparticles on pig tendon tissue as set forth in Example 15.
Figure 12:
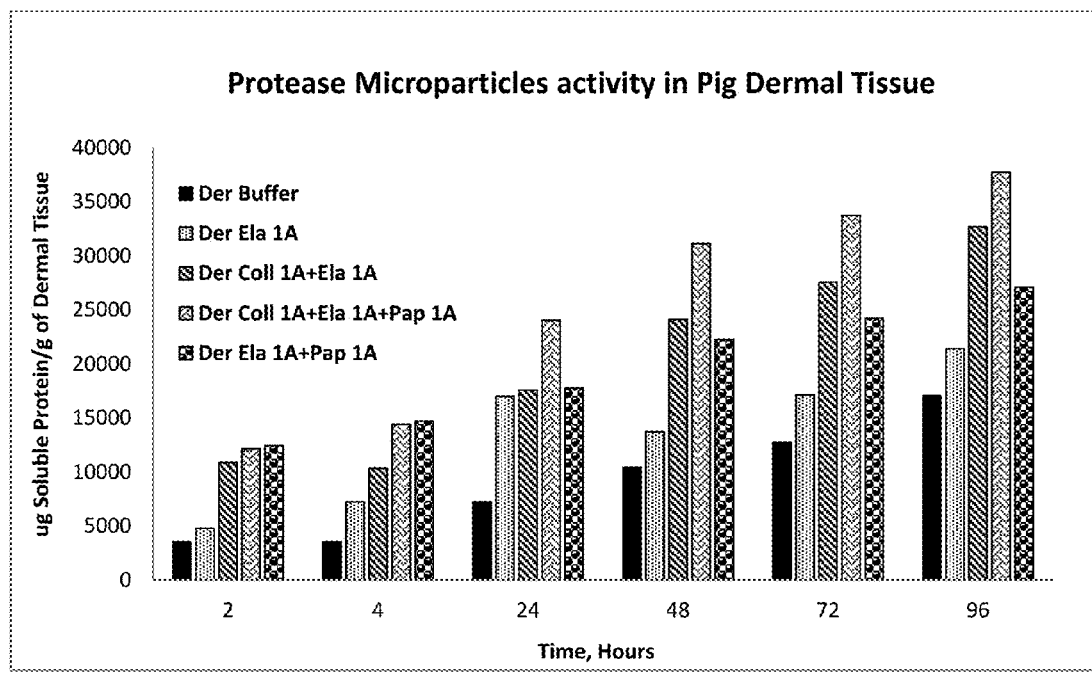
FIG. 12 shows protease activity of elastase microparticle alone and combination with other protease containing microparticles on pig dermal tissue as set forth in Example 15.
Figure 13:
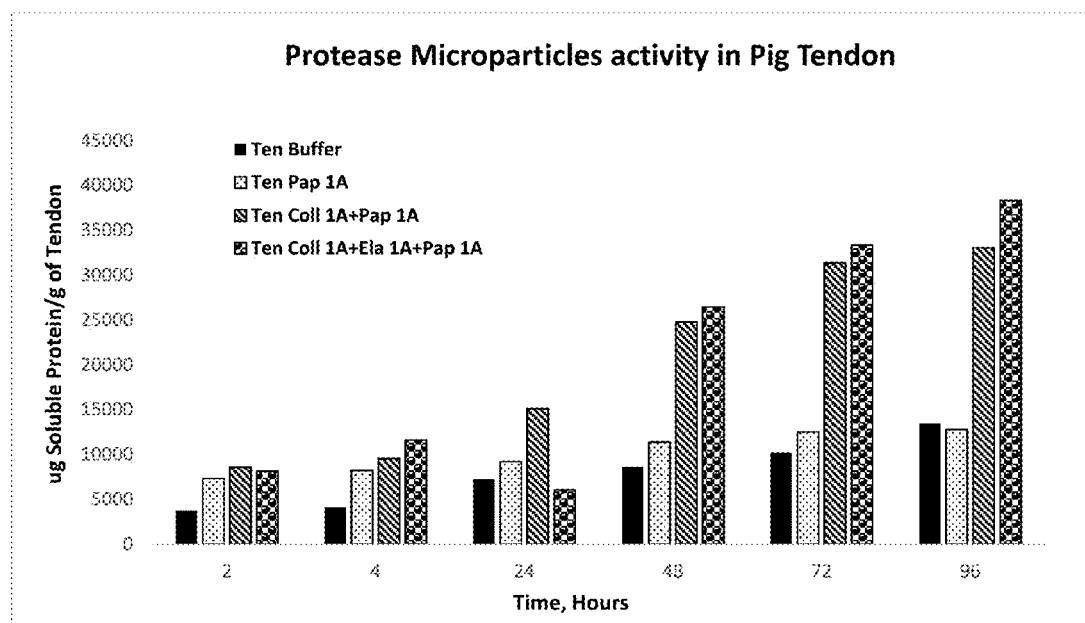
FIG. 13 shows protease activity of papain microparticle alone and combination with other protease containing microparticles on pig tendon tissue as set forth in Example 15.

The unexpected synergistic activity of protease enzymes in microparticle form was further studied in a more comprehensive study where a larger number of combinations were studied over a period of 96 hours. The results of this study confirm that the synergistic action of protease enzymes is observed. As can be seen in FIG. 11, the combination of elastase protease enzyme microparticles show a much higher activity than the individual protease enzymes as microparticles. FIG. 12 shows the same study carried out in the pig dermal collagen, once again showing that the combination enzyme microparticles work better than individual microparticles. FIG. 13 shows a study of the comparison of papain microparticles alone and in combination of microparticles of the other enzymes. Once again, the combination microparticles show up to 208% increase in enzyme activity when all 3 enzyme microparticles are present in the system as compared to the papain microparticles alone. Together, these studies show that in a variety of collagen sources, protease enzymes work better when added in combination as slow release microparticles than when added alone as slow release microparticles.

Example 16

In this Example, Pap 1A of Example 2 which was prepared with polymer with an average molecular weight of about 10 kilo Dalton was compared to Pap 3A of Example 3 which was prepared with polymer with an average molecular weight of about 25 kilo Dalton. The activity is expressed as the amount of soluble protein per gram of collagen tissue as a function of time. Similarly, Elastase 1A of example 2 which was prepared with polymer with an average molecular weight of about 10 kilo Dalton was compared to Elastase 3A of Example 3 which was prepared with polymer with an average molecular weight of about 25 kilo Dalton. The activity is expressed as the amount of soluble protein per gram of collagen tissue as a function of time.

Figure 14:
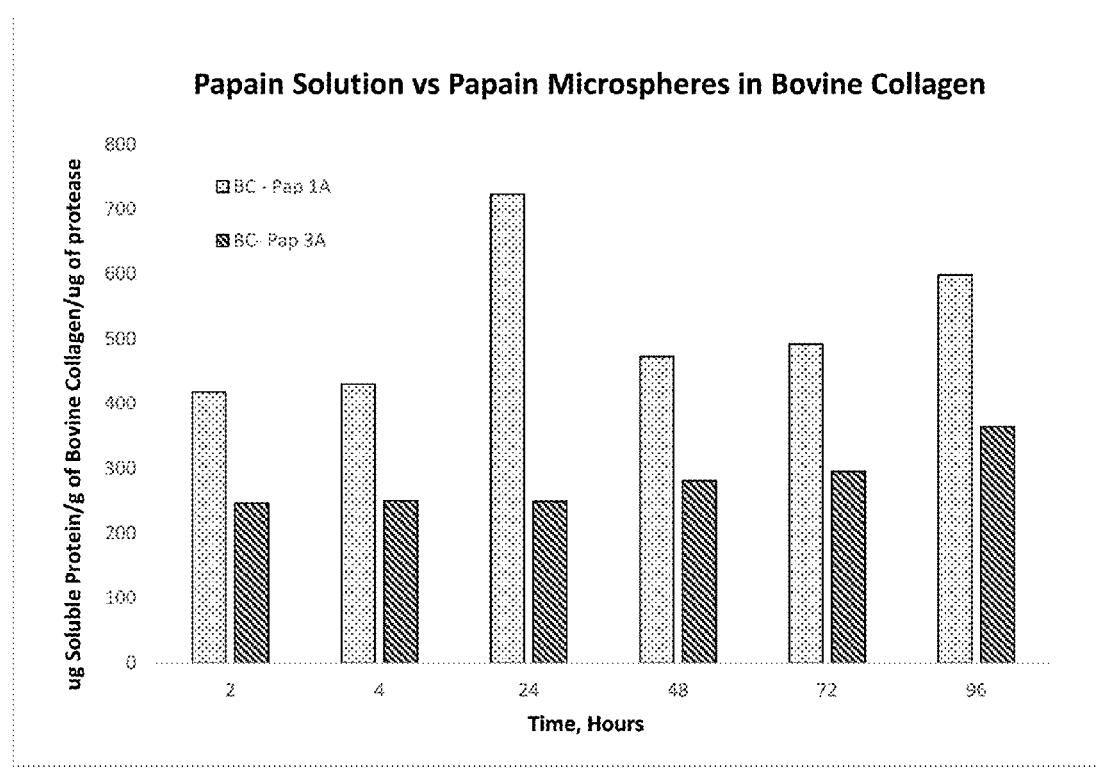
FIG. 14 shows the effect of molecular weight of biodegradable polymer on protease activity of papain microparticles prepared with of different molecular weights of polylactides-polyglycolic acid polymer on bovine collagen tissue as set forth in Example 16.
Figure 15:
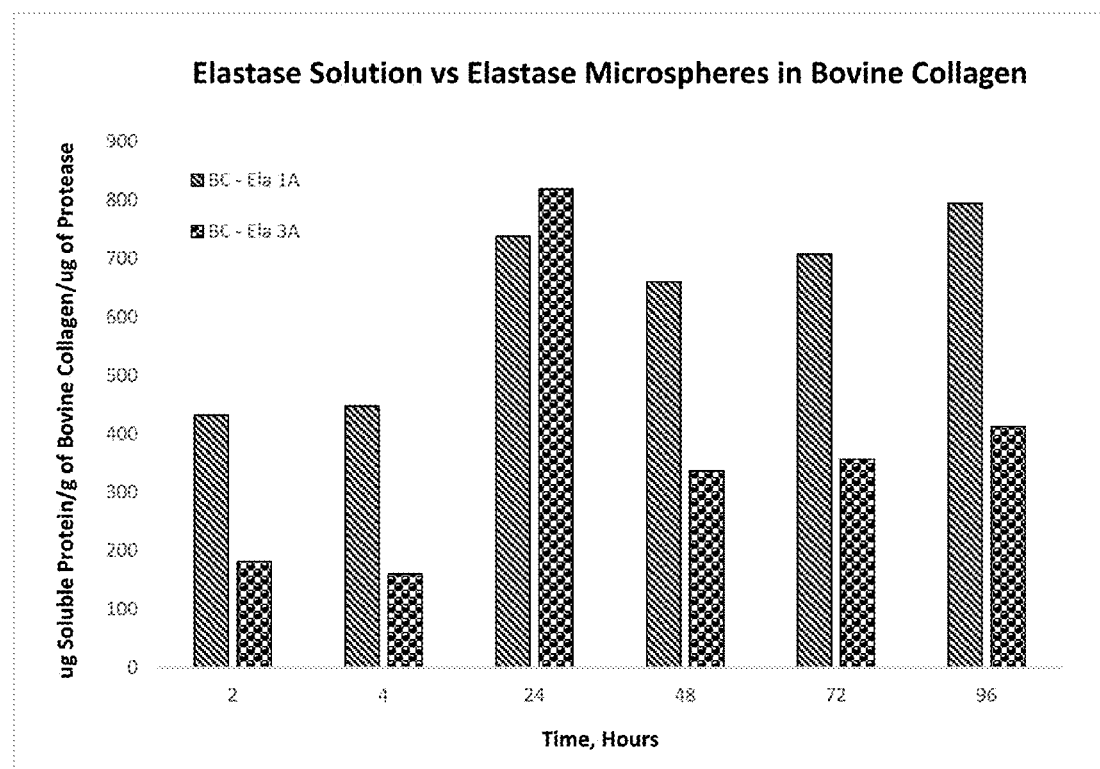
FIG. 15 shows the effect of molecular weight of biodegradable polymer on protease activity of elastase microparticles prepared with of different molecular weights of polylactides-polyglycolic acid polymer on bovine collagen tissue as set forth in Example 16.

FIG. 14 shows the protease activity of papain from 1A and 3A polymers. The activity from 1A polymer (low molecular weight grade) is higher and starts faster than the activity from higher molecular weight polymer. The release of the papain from the higher molecular weight polymer is lower but is released over a longer period of time. This is an example of one way in which the protease activity profile can be varied using differing molecular weight polymers. FIG. 15 shows the protease activity of elastase from 1A and 3A polymers. As was the case with the papain, the elastase activity from 1A polymer (low molecular weight grade) is higher and starts faster than the activity from higher molecular weight polymer which has a prolonged delivery profile.

Example 17

A ready to use final composition for treatment is prepared by mixing appropriate amounts of each microparticle alone or in combination with each other, along with one or more inactive ingredients. Examples of inactive ingredients include suspending agents such as carboxymethyl cellulose and other such water soluble polymers, polyhydric sugars such as mannitol, and wetting agent such as a non-ionic surfactant, as needed. A suitable method of sterilization is used to obtain a sterile dry material that is reconstituted with a suitable aqueous solvent prior to injection. Examples of such compositions comprise of the following:

A vial containing lyophilized collagenase microparticles is made containing from about 50 to about 150 units of collagenase activity along with 5-20 mg of carboxymethyl cellulose, 50-200 mg of mannitol and 5-20 mg of polyvinyl pyrrolidone. This composition may also contain microparticles containing dexamethasone or another similar anti-inflammatory agent containing 2-10 mg of the active medicament.

A vial containing lyophilized elastase microparticles containing from about 0.1 to about 0.5 units of elastase activity along with 5-20 mg of carboxymethyl cellulose, 50-200 mg of mannitol and 5-20 mg of polyvinyl pyrrolidone. This composition may also contain microparticles containing dexamethasone or another similar anti-inflammatory agent containing 2-10 mg of the active medicament.

A vial containing lyophilized papain microparticles containing from about 1 to about 5 units of papain activity along with 5-20 mg of carboxymethyl cellulose, 50-200 mg of mannitol and 5-20 mg of polyvinyl pyrrolidone. This composition may also contain microparticles containing dexamethasone or another similar anti-inflammatory agent containing 2-10 mg of the active medicament.

A vial containing lyophilized collagenase microparticles containing from about 50 to about 150 units of collagenase activity, from about 0.1 to about 0.5 units of elastase activity, from about 1 to about 5 units of papain activity, along with 5-20 mg of carboxymethyl cellulose, 50-200 mg of mannitol and 5-20 mg of polyvinyl pyrrolidone. This composition may also contain microparticles containing dexamethasone or another similar anti-inflammatory agent containing 2-10 mg of the active medicament.

The invention claimed is:

1. A composition, comprising a plurality of biodegradable polymer microparticies comprising a protease enzyme therein, the biodegradable polymer and the protease enzyme forming a controlled release matrix for extended release of the enzyme; wherein (a) the protease is selected from the group consisting of collagenase, papain, elastase and mixtures thereof; (b) the plurality of the biodegradable polymer microparticies is a mixture of biodegradable polymer microparticles containing different proteases; (c) a first portion of the plurality of the biodegradable polymer microparticles contains collagenase, and (d) a second portion of the plurality of the biodegradable polymer microparticles contains papain or elastase.

2. The composition of claim 1, wherein the biodegradable polymer is selected from the group consisting of polylactic acid (PLA), polylactic co-glycolic acid (PLGA), polygiycolic acid (PGA) polylactones, polyorthocarbonate, polyhydroxybutyrate, polyalkylcyanoacrylates, polyanhydrides, polyorthoesters, polyester, polyamide, polyglycolides (PGA), polyorthoester, polyacetates, polystyrene, polycarbonates, polysaccharides, polycaprolactone, L-polylactides, block co-polymers of polyesters and linear or star-polyethyleneglycol, poly-beta-hydroxybutyrate, beta-hydroxyvalerate-copolymers, polyaminoacids, hydrophobized hyaluronic acid, dextrans, starches, methyl methacrylate, acrylamide, bisacrylamide, albumin, cellulose, cellulose-based polymers, chitosan, collagen, gelatin, proteins, Polyvinyl alcohol (PVA), polyvinylpyrrolidone, polyvinylpyridine, and ethylene glycol polymers.

3. The composition of claim 2, wherein the biodegradable polymer is polylactic co-glycolic acid or polylactic acid.

4. The composition of claim 3, wherein the biodegradable polymer is poly lactide-poly glycolide polymer copolymer (PLGA).

5. The composition of claim 4, wherein the PLGA has a molecular weight of from about 7,000 to about 100,000.

6. The composition of claim 1, wherein the microparticles have a cross-sectional diameter of from about 10 nm to about 100 μm.

7. The composition of claim 6, wherein the microparticles have a cross-sectional diameter of from about 100 nm to about 50 μm.

8. The composition of claim 7, wherein the microparticles have a cross-sectional diameter of from about 1 μm to about 20 μm.

9. The composition of claim 1, wherein the percent loading of the protease in the microparticles is from about 0.1 to about 5.0.

10. The composition of claim 9, wherein the protease is collagenase and the percent loading of the protease in the microparticles is from about 3 to about 5%.

11. The composition of claim 9, wherein the protease is elastase and the percent loading of the protease in the microparticles is from about 0.1 to about 0.6%.

12. The composition of claim 9, wherein the protease is papain and the percent loading of the protease in the microparticles is from about 0.5 to about 0.9.

13. A composition comprising a plurality of biodegradable polymer microparticles comprising a protease enzyme therein, the biodegradable polymer and the protease enzyme forming a controlled release matrix for extended release of the enzyme; wherein (a) the protease is selected from the group consisting of collagenase, papain; elastase and mixtures thereof; (b) the plurality of biodegradable polymer microparticles is a mixture of biodegradable polymer microparticles containing different proteases; (c) a first portion of the plurality of the biodegradable polymer microparticles contains collagenase, (d) a second portion of the plurality of the biodegradable polymer microparticles contains papain and (e) a third portion of the biodegradable polymer microparticles contains elastase.

14. The composition of claim 1, further comprising an auxiliary therapeutic agent dissolved or dispersed within the controlled release matrix.

15. The composition of claim 14, wherein the auxiliary therapeutic agent is co-mingled with the microparticles in the composition.

16. The composition of claim 14, wherein the auxiliary therapeutic agent is a steroidal or a non-steroidal inflammation reducing agent.

17. The composition of claim 16, wherein the steroidal inflammation reducing agent is dexamethasone.

18. A method of treating hypertrophic scars (or tissue) in a mammal, comprising administering an effective amount of a composition of claim 1 to a mammal in need thereof.

19. The method of claim 18, wherein said hypertrophic scar is a keloid.

20. The method of claim 18, wherein the administering is carried out by injecting the composition into an area requiring said treatment or by topically applying the composition to an area requiring said treatment.

21. The method of claim 18, wherein the composition is administered once a week, once a month or once every two months.

* * * * *